United States Patent
Gauthier

(10) Patent No.: US 11,607,392 B2
(45) Date of Patent: Mar. 21, 2023

(54) ENCAPSULATION SYSTEM FOR PROLONGED RELEASE OF ACTIVE AGENTS

(71) Applicant: TREND INNOVATIONS, Montreal (CA)

(72) Inventor: Jean-Francois Gauthier, Orford (CA)

(73) Assignee: TREND INNOVATIONS, Boucherville (CA)

(*) Notice: Subject to any disclaimer, the term of this patent is extended or adjusted under 35 U.S.C. 154(b) by 0 days.

(21) Appl. No.: 16/648,390

(22) PCT Filed: Sep. 18, 2018

(86) PCT No.: PCT/IB2018/057171
§ 371 (c)(1),
(2) Date: Mar. 18, 2020

(87) PCT Pub. No.: WO2019/053689
PCT Pub. Date: Mar. 21, 2019

(65) Prior Publication Data
US 2020/0297648 A1     Sep. 24, 2020

Related U.S. Application Data

(60) Provisional application No. 62/560,746, filed on Sep. 20, 2017, provisional application No. 62/559,877, filed on Sep. 18, 2017.

(51) Int. Cl.
*A61K 9/50* (2006.01)
*A61K 36/28* (2006.01)
*A61K 36/45* (2006.01)
*B01J 13/04* (2006.01)

(52) U.S. Cl.
CPC ............ *A61K 9/5015* (2013.01); *A61K 36/28* (2013.01); *A61K 36/45* (2013.01); *B01J 13/043* (2013.01)

(58) Field of Classification Search
None
See application file for complete search history.

(56) References Cited

U.S. PATENT DOCUMENTS

| 3,565,559 A * | 2/1971 | Sato et al. ............... B01J 13/08 264/4.4 |
| 6,495,161 B1 | 12/2002 | Soon-Shiong et al. |
| 7,758,888 B2 * | 7/2010 | Lapidot ................... A61P 31/04 424/489 |
| 2001/0018072 A1 * | 8/2001 | Unger ................... A61K 9/5115 514/23 |
| 2010/0173002 A1 | 7/2010 | Yulai et al. |
| 2014/0031463 A1 * | 1/2014 | Kempter ................. A23L 27/72 524/127 |
| 2014/0341958 A1 * | 11/2014 | Gosselin .............. A61K 8/9789 424/401 |
| 2017/0002302 A1 * | 1/2017 | Dihora ................... C11D 3/505 |
| 2017/0245493 A1 * | 8/2017 | Gezundhait ............ A01N 25/34 |

FOREIGN PATENT DOCUMENTS

EP           1702675           9/2006

OTHER PUBLICATIONS

PubChem "Menthyl salicylate," printed 2022 (Year: 2022).*
Derwent abstract, CN 1634095 A, printed 2022 (Year: 2022).*
Sigma "Particle size conversion table," accessed 2022 (Year: 2022).*
International Search Report and Written Opinion issued in corresponding application No. PCT/IB2018/057171 dated Jan. 15, 2019.

* cited by examiner

*Primary Examiner* — David J Blanchard
*Assistant Examiner* — Alissa Prosser
(74) *Attorney, Agent, or Firm* — BCF LLP

(57) ABSTRACT

The present technology generally relates to an encapsulation system for delivery of an active agent, the encapsulation system comprising a matrix of microcapsules, wherein a first portion of microcapsules in the matrix of microcapsules has an average diameter of from about 0.1 microns to about 10 microns; a second portion of the microcapsules has an average diameter of from about 10 microns to about 100 microns; and a third portion of the microcapsules has an average diameter of from about 100 microns to about 500 microns; and wherein the active agent is encapsulated in the microcapsules.

10 Claims, 10 Drawing Sheets

| | Knee | Elbow | Shoulder | Back | Ankle | Wrist |
|---|---|---|---|---|---|---|
| Number of treated subjects | 65 | 54 | 35 | 34 | 27 | 27 |
| Positive results | 63 | 54 | 32 | 30 | 27 | 27 |
| % efficiency | 97% | 100% | 91% | 88% | 100% | 100% |

ENCAPSULATION SYSTEM FOR PROLONGED RELEASE OF ACTIVE AGENTS

CROSS-REFERENCE TO RELATED APPLICATIONS

This application claims the benefit of and priority to U.S. provisional patent application No. 62/559,877, filed on Sep. 18, 2017; and to U.S. provisional patent application No. 62/560,746, filed on Sep. 20, 2017, the content of both which is herein incorporated in entirety by reference.

TECHNICAL FIELD

The present technology generally relates to encapsulation systems for encapsulation of active agents and for prolonged release of the encapsulated active agents and to methods for producing such encapsulation systems. The present technology also generally relates to supports comprising the encapsulation systems. The present technology also further relates to methods for impregnating and/or fixing the encapsulation systems to the supports.

BACKGROUND OF TECHNOLOGY

Encapsulation of active agents is a common practice in the biotechnology, pharmaceutical and cosmetic industries to, inter alia, increases the stability and shelf-life of the encapsulated active agents as well as to control its delivery. Typically, the encapsulation system confers a protective layer against adverse environment conditions and contributes to regulating or controlling the release of the encapsulated active agents.

Impregnation of encapsulation systems into supports such as textiles, fabrics, sponges or the like has been proposed in order to extend the period during which a substrate such as the skin of a subject is in contact with encapsulation systems comprising an active agent to be delivered to the substrate.

However, encapsulation systems that have been proposed and supports having such encapsulation systems are only capable of releasing a limited amount of the active agent over a limited period of time, such as for example, over a couple of days. As such, there remains a need for encapsulation systems and for support systems that allow for prolonged release of encapsulated active agents.

SUMMARY OF DISCLOSURE

According to various aspects, the present technology relates to an encapsulation system for delivery of an active agent, the encapsulation system comprising a matrix of microcapsules, wherein a first portion of microcapsules in the matrix of microcapsules has an average diameter of from about 0.1 microns to about 10 microns; a second portion of the microcapsules has an average diameter of from about 10 microns to about 100 microns; and a third portion of the microcapsules has an average diameter of from about 100 microns to about 500 microns; and wherein the active agent is encapsulated in the microcapsules.

According to various aspects, the present technology relates to an encapsulation system for delivery of an active agent, the encapsulation system comprising a matrix of microcapsules, wherein a first portion of microcapsules in the matrix of microcapsules has an average diameter of from about 0.05 microns to about 1 microns; a second portion of the microcapsules has an average diameter of from about 1 microns to about 10 microns; and a third portion of the microcapsules has an average diameter of from about 10 microns to about 50 microns; and wherein the active agent is encapsulated in the microcapsules.

According to various aspects, the present technology relates to a support for delivery of an active agent to a subject, the support comprising an encapsulated system distributed in at least a portion of the support, the encapsulation system comprising a matrix of microcapsules, wherein a first portion of microcapsules in the matrix of microcapsules has an average diameter of from about 0.1 microns to about 10 microns; a second portion of the microcapsules has an average diameter of from about 10 microns to about 100 microns; and a third portion of the microcapsules has an average diameter of from about 100 microns to about 500 microns; wherein the active agent is encapsulated in the microcapsules; and wherein the support releases the active agent for at least about 100 hours.

According to various aspects, the present technology relates to a support for delivery of an active agent to a subject, the support comprising an encapsulated system distributed in at least a portion of the support, the encapsulation system comprising a matrix of microcapsules, wherein a first portion of microcapsules in the matrix of microcapsules has an average diameter of from about 0.05 microns to about 1 microns; a second portion of the microcapsules has an average diameter of from about 1 microns to about 10 microns; and a third portion of the microcapsules has an average diameter of from about 10 microns to about 50 microns; wherein the active agent is encapsulated in the microcapsules; and wherein the support releases the active agent for at least about 100 hours.

Embodiments and Implementations of the present technology each have at least one of the above-mentioned aspects and/or features, but do not necessarily have all of them. It should be understood that some aspects of the present technology that have resulted from attempting to attain the above-mentioned object may not satisfy this object and/or may satisfy other objects not specifically recited herein.

Additional and/or alternative features, objects, aspects and advantages of implementations of the present technology will become apparent from the following description, the accompanying drawings as well as the appended claims.

BRIEF DESCRIPTION OF DRAWINGS

A detailed description of embodiments of the present disclosure is provided below, by way of example only, with reference to the accompanying drawings, in which:

FIG. 2A shows an encapsulation system with an ordered arrangement of the microcapsules; FIG. 2B shows an encapsulation system with a disordered arrangement of the microcapsules;

Figure 4:
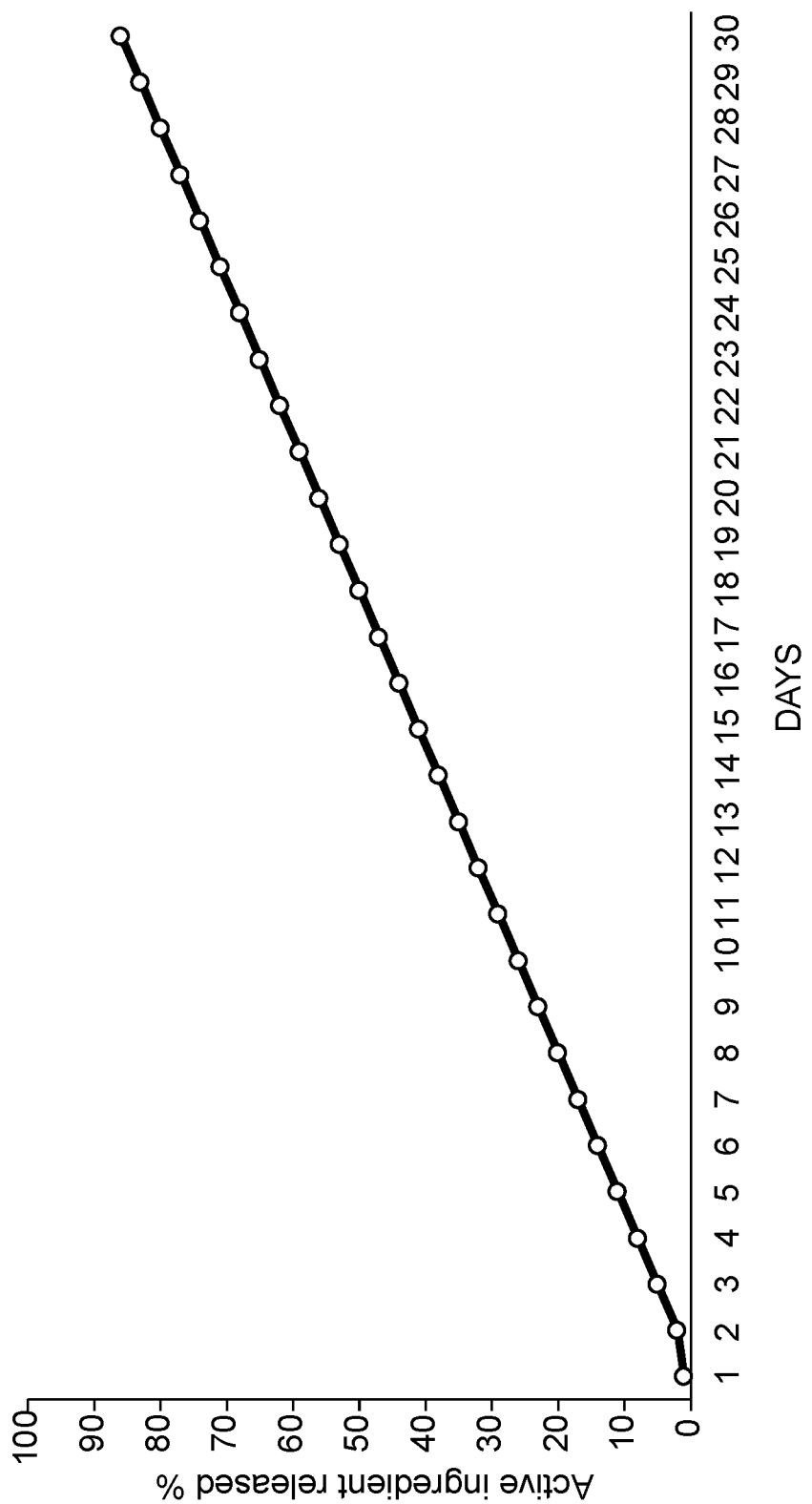
Figure 5:
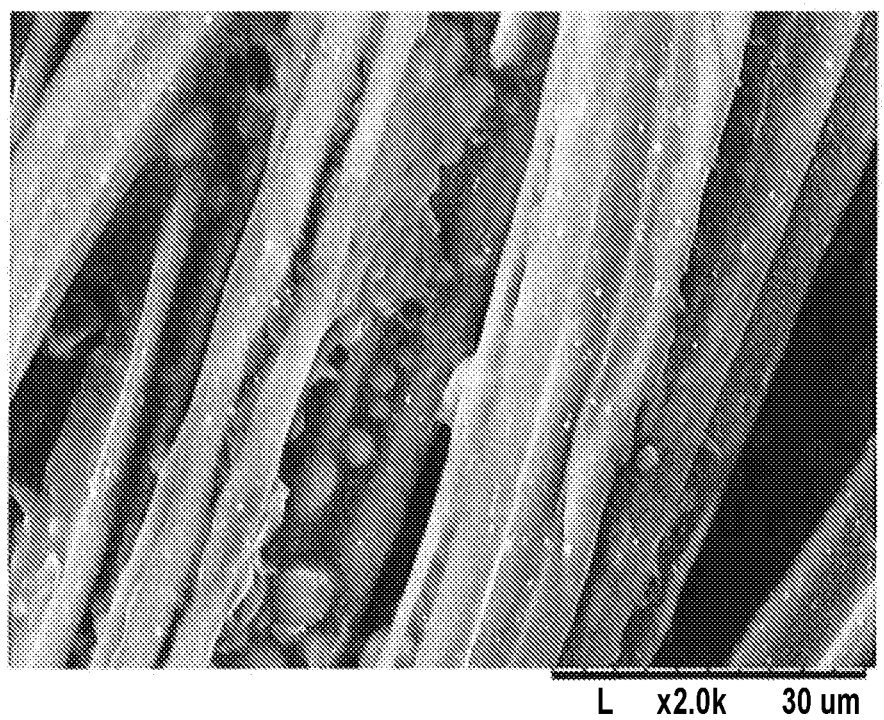

and (5) represents the treated textile support onto which the encapsulation system has been applied (treated textile support);

FIG. 4 shows a graph indicating the rate of release of an active agent from the encapsulation system according to one embodiment of the present disclosure over time;

FIG. 5 shows a picture of fibers from a treated textile support according to one embodiment of the present disclosure that has been submitted to 180 minutes of a pilling test performed according to ASTM D3512 standards.

Figure 6A:
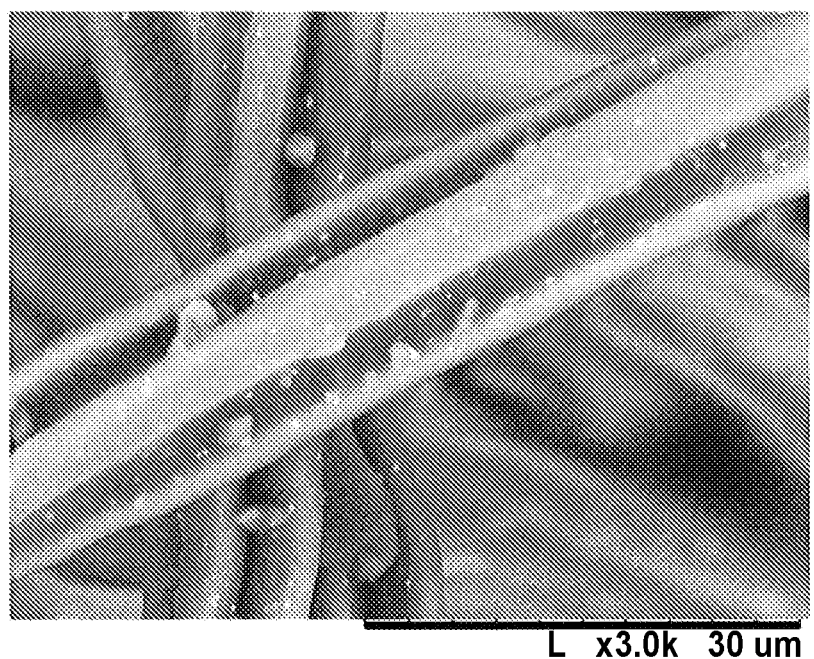
Figure 6B:
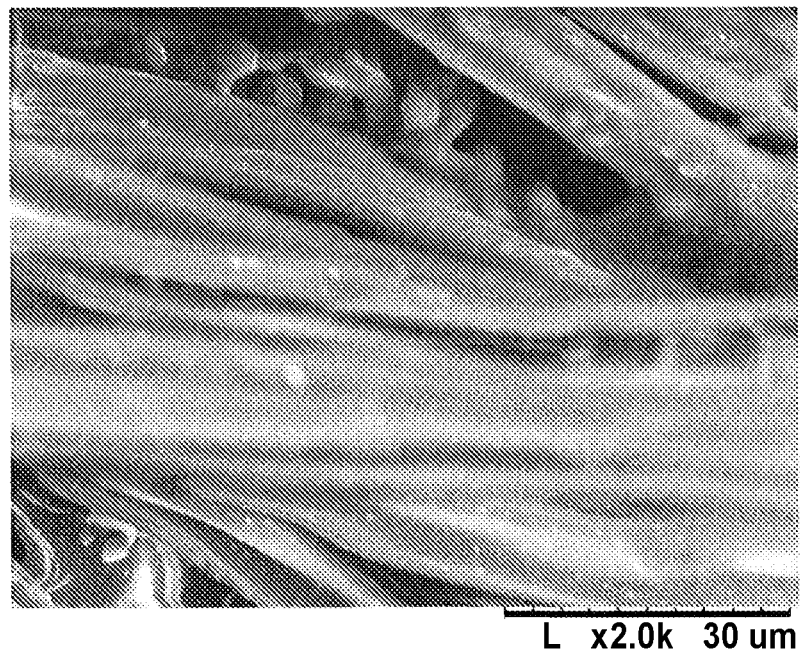
Figure 6C:
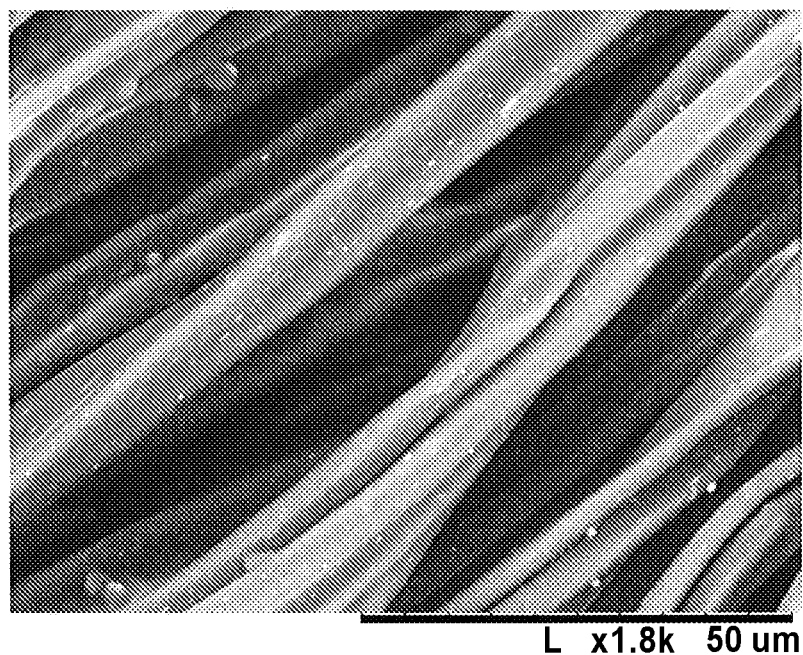
Figure 6D:
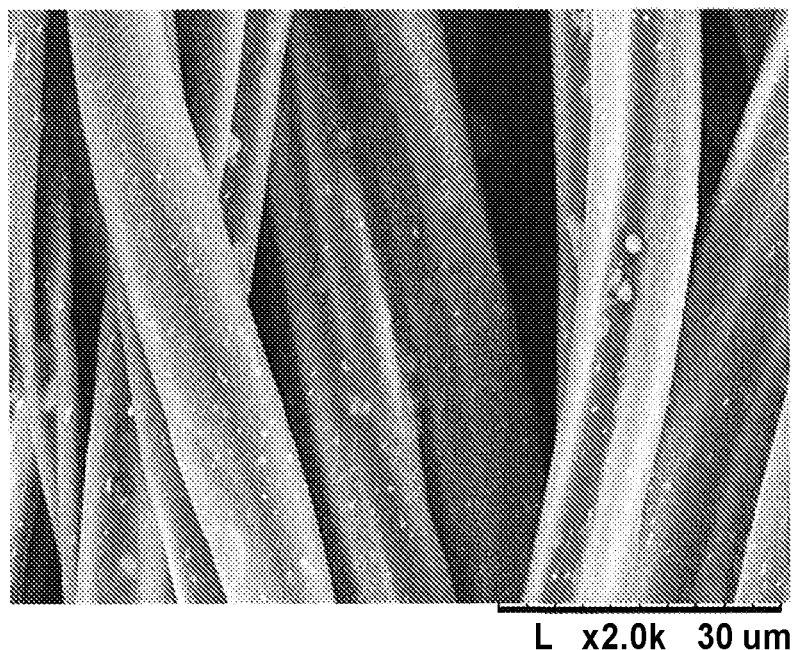

FIGS. 6A-6E show pictures of fibers from a treated textile support according to one embodiment of the present disclosure submitted to various cycles of washing/drying. FIG. 6A: treated textile support prior to initial cycle of washing/drying; FIG. 6B: treated textile support after 5 cycles of washing/drying; FIG. 6C: treated textile support after 10 cycles of washing/drying; FIG. 6D: treated textile support after 15 cycles of washing/drying; and FIG. 6E: treated textile support after 20 cycles of washing/drying.

Figure 7:
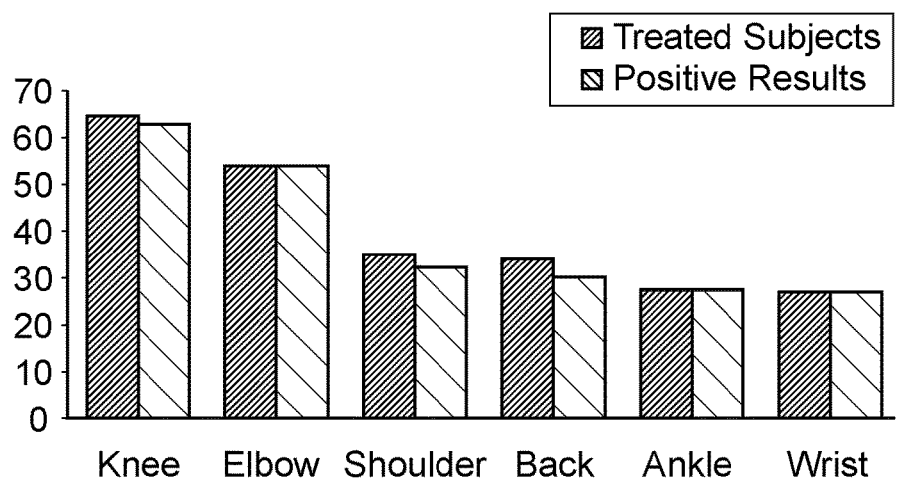

FIG. 7 shows a graph indicating the efficiency of the encapsulation system according to one embodiment of the present disclosure in delivering active agents to a subject afflicted with pain at the indicated areas.

Figure 8:
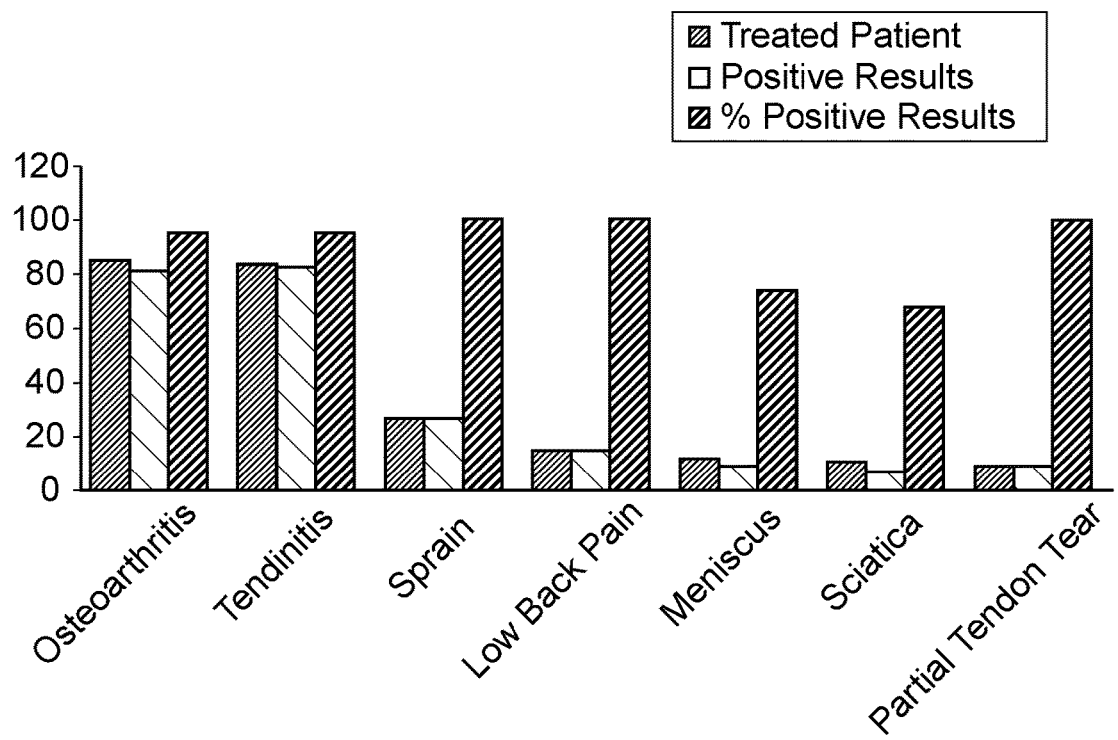

FIG. 8 shows a graph indicating the efficiency of the encapsulation system according to one embodiment of the present disclosure in delivering active agents to a subject afflicted with the indicated conditions.

DETAILED DESCRIPTION OF TECHNOLOGY

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant technology. Hence, the following specification is intended to illustrate some particular embodiments of the technology, and not to exhaustively specify all permutations, combinations and variations thereof.

As used herein, the singular form "a," "an" and "the" include plural referents unless the context clearly dictates otherwise.

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

i) Encapsulation System

In one embodiment, the present technology relates to an encapsulation system for encapsulating active agents. In some implementations of this embodiment, the encapsulation system exhibits prolonged release properties. In some other implementations of this embodiment, the encapsulation system exhibits sustained release properties. In some further implementations of this embodiment, the encapsulation system exhibits prolonged and sustained release properties.

The encapsulation system of the present technology comprises a plurality of microcapsules. As used herein, the term "microcapsule" refers to hollow microparticle composed of a microcapsule shell ("shell") surrounding a core-forming space ("inner core") available to permanently or temporarily entrapped or encapsulate active agents (e.g., drugs, pesticides, cosmetics, dyes, or the like). As such, the active agents to be encapsulated in the encapsulation system are substantially located in the inner core of the microcapsules. The microcapsules are said to be "loaded" when they encapsulate or comprise an active agent and are said to be "unloaded" when they do not encapsulate or comprise an active agent.

As used herein, the expression "prolonged release" refers to the release of an active agent over an extended period of time. As used herein, the expression "sustained release" refers to the release of an active agent steadily over an extended period of time.

Figure 1A:
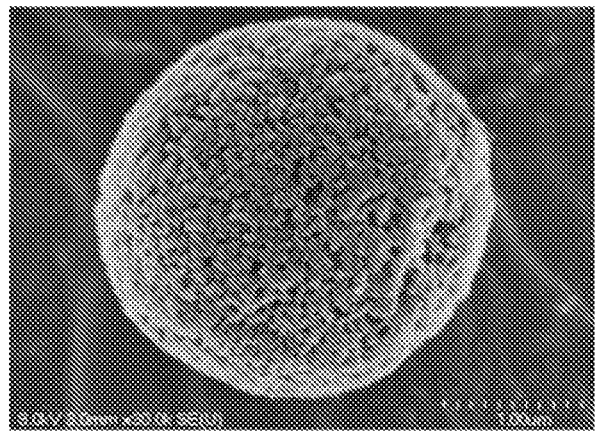
FIG. 1 is picture of a microcapsule according to one embodiment of the present technology; panel A represents an intact microcapsule, whereas panel B represents a ruptured microcapsule.
Figure 1B:
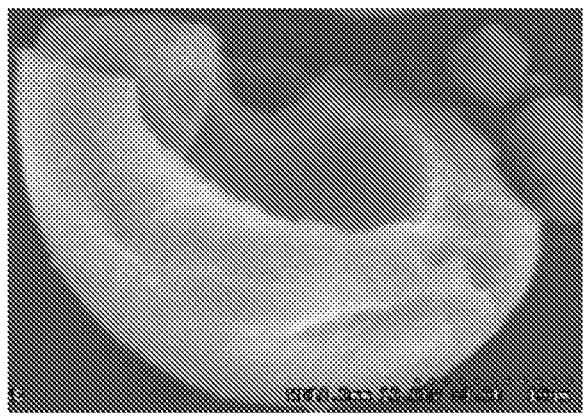

The microcapsules of the present technology release the active agent encapsulated in their inner core over time by, for example, rupture of the microcapsule, whereby the active agent is released when sufficient pressure or shear action is applied to the microcapsules and the shell is broken, or by diffusion of the active agent, whereby the shell of the microcapsule is porous allowing the active agent to diffuse through the shell and out of the microcapsule accompanied or not by dissolution of the shell of the microcapsule (FIG. 1).

Figure 2A:
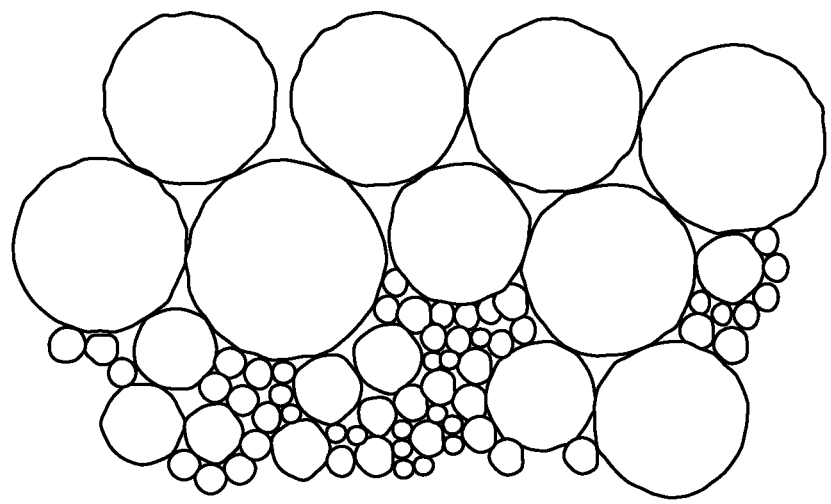
FIGS. 2A-2B are schematic representations of an encapsulation system according to one embodiment of the present technology.
Figure 2B:
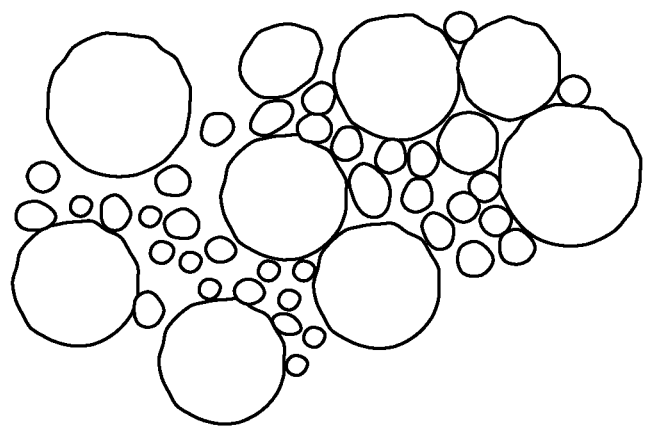

In some instances, the encapsulation system comprises a matrix of microcapsules. As used herein, the term "matrix" refers to an array of microcapsules, wherein the microcapsules are of various sizes (e.g., various diameters). The matrix of microcapsules may display an ordered arrangement of the microcapsules wherein the largest microcapsules (i.e., larger diameters) are arranged next to each other and the smaller microcapsules (i.e., smaller diameters) are arranged within the space created between the large microcapsules (FIG. 2A). The matrix of microcapsules may also display a disordered arrangement of microcapsules wherein the largest microcapsules (i.e., larger diameters) and the smaller microcapsules (i.e., smaller diameters) are randomly distributed (FIG. 2B).

The microcapsules of the present technology have all three dimensions in the range of from about 0.05 microns to about 1000 microns, or from about 0.05 microns to 500 microns, or from about 0.05 microns to about 100 microns, or from about 0.05 microns to about 50 microns, or from about 0.05 microns to about 25 microns, or from about 0.1 microns to about 1000 microns, or from about 0.1 microns to about 500 microns, or from about 0.1 microns to about 475 microns, or from about 0.1 microns to about 450 microns, or from about 0.1 microns to about 425 microns, or from about 0.1 microns to about 400 microns, or from about 0.1 microns to about 375 microns, or from about 0.1 microns to about 350 microns, or from about 0.1 microns to about 325 microns, or from about 0.1 microns to about 300 microns, or from about 0.1 microns to about 275 microns, or from about 0.1 microns to about 250 microns, or from about 0.1 microns to about 225 microns, or from about 0.1 microns to about 200 microns, or from about 0.1 microns to about 190 microns, or from about 0.1 microns to about 180 microns, or from about 0.1 microns to about 170 microns, or from about 0.1 microns to about 160 microns, or from about 0.1 microns to about 150 microns, or from about 0.1 microns to about 140 microns, or from about 0.1 microns to about 130 microns, or from about 0.1 microns to about 120 microns, or from about 0.1 microns to about 110 microns, or from about 0.1 microns to about 100 microns, or from about 0.1 microns to about 90 microns, or from about 0.1 microns to about 80 microns, or from about 0.1 microns to about 70 microns, or from about 0.1 microns to about 60 microns, or from about 0.1 microns to about 50 microns, or from about 0.1 microns to about 40 microns, or from about 0.1 microns to about 30 microns, or from about 0.1 microns to about 20 microns, or from about 0.1 microns to about 10 microns, or from about 0.1 microns to about 5 microns, or from about 0.1 microns to about 2 microns, or from about 0.1 microns to about 1 micron, or from about 0.1 microns to about 0.5 microns, or from about 0.5 microns to about 1000 microns, or from about 0.5 microns to about 500 microns, or from about 0.5 microns to about 475 microns, or from about 0.5 microns to about 425 microns, or from about 0.5 microns to about 425 microns, or from about 0.5 microns to about 400 microns, or from about 0.5 microns to about 375 microns, or from about 0.5 microns to about 350 microns, or from about 0.5 microns to about 325 microns, or from about 0.5 microns to about 300 microns, or from about 0.5 microns to about 275 microns, or from about 0.5 microns to about 250 microns, or from about 0.5 microns to about 225 microns, or from about 0.5 microns to about 200 microns, or from about 0.5 microns to about 190 microns, or from about 0.5 microns to about 180 microns, or from about 0.5 microns to about 170 microns, or from about 0.5 microns to about 160 microns, or from about 0.5 microns to about 150 microns, or from about 0.5 microns to about 140 microns, or from about 0.5 microns to about 130 microns, or from about 0.5 microns to about 120 microns, or from about 0.5 microns to about 110 microns, or from about 0.5 microns to about 100 microns, or from about 0.5 microns to about 90 microns, or from about 0.5 microns to about 80 microns, or from about 0.5 microns to about 70 microns, or from about 0.5 microns to about 60 microns, or from about 0.5 microns to about 50 microns, or from about 0.5 microns to about 40 microns, or from about 0.5 microns to about 30 microns, or from about 0.5 microns to about 20 microns, or from about 0.5 microns to about 15 microns, or from about 0.5 microns to about 10 microns, or from about 0.5 microns to about 5 microns, or from about 0.5 microns to about 2 microns, or from about 0.05 microns to about 50 microns, or from about 0.05 microns to about 40 microns, or from about 0.05 microns to about 30 microns, or from about 0.05 microns to about 25 microns, or from about 0.05 microns to about 20 microns, or from about 0.05 microns to about 15 microns, or from about 0.05 microns to about 10 microns, or from about 0.05 microns to about 5 microns, or from about 0.05 microns to about 2 microns; or about 5 microns to about 20 microns; or about 6 microns, or about 7 microns, or about 8 microns, or about 9 microns, or about 10 microns.

Preferably, all three dimensions of the microcapsules permit dispersion of an active agent within the microcapsules and allow retention of the microcapsules in or on a support onto which the microcapsules are applied, such as for example, in the interstices, pores or cross linkage openings in a support, or onto the support itself (e.g., onto the fibers of a textile) or absorbed into the support (e.g., absorbed into the fibers of a textile). Microcapsules may be visualized using techniques such as, but not limited to, extraction method with tracer techniques (e.g., electron microscopy). Other techniques to visualize microcapsules will be known to those of skill in the art. The size of the microcapsules is determined by techniques well known in the art, such as, but not limited to, photon correlation spectroscopy, laser diffractometry, scanning electron microscopy and/or 3CCD (charged-couple device).

In some implementations, the matrix comprises a plurality of microcapsules wherein a first portion of the microcapsules have an average diameter of from about 0.1 microns to about 10 microns; a second portion of the microcapsules have an average diameter of from about 10 microns to about 100 microns; a third portion of the microcapsules have an average diameter of from about 100 microns to about 500 microns.

In some implementations, the matrix comprises a plurality of microcapsules wherein a first portion of the microcapsules have an average diameter of from about 0.05 microns to about 1 microns; a second portion of the microcapsules have an average diameter of from about 1 microns to about 10 microns; a third portion of the microcapsules have an average diameter of from about 10 microns to about 50 microns.

In some implementations, the matrix comprises a plurality of microcapsules wherein a first portion of the microcapsules have an average diameter of from about 0.1 microns to about 1 microns; a second portion of the microcapsules have an average diameter of from about 1 microns to about 10 microns; a third portion of the microcapsules have an average diameter of from about 10 microns to about 100 microns; and fourth portion of the microcapsules have an average diameter of from about 100 microns to about 500 microns.

In some implementations, the matrix comprises a plurality of microcapsules wherein a first portion of the microcapsules have an average diameter of from about 0.1 microns to about 1 microns; a second portion of the microcapsules have an average diameter of from about 1 microns to about 5 microns; a third portion of the microcapsules have an average diameter of from about 5 microns to about 25 microns; a fourth portion of the microcapsules have an average diameter of from about 25 microns to about 100 microns; and a fifth portion of the microcapsules have an average diameter of from about 100 microns to about 500 microns.

Methods and techniques for measuring the diameter of microcapsules are well-known in the art.

The shell of the microcapsule of the present technology may comprise a plurality of pores having diameters of from about 1 nm to about 100 nm; or from about 1 nm to about 75 nm, or from about 1 nm to about 50 nm, or from about 1 nm to about 100 nm, or from about 2 nm to about 75 nm, or from about 2 nm to about 50 nm.

In some instances, the inner core of an unloaded microcapsule is gaseous, hollow or is a vacuum.

In some instances, the shell of the microcapsules has an average thickness of between about 50 nm to 500 microns.

The surface area of the microcapsules of the present technology is from about 100 $m^2/g$ to about 1000 $m^2/g$, or from about 100 $m^2/g$ to about 900 $m^2/g$, or from about 100 $m^2/g$ to about 800 $m^2/g$, or from about 100 $m^2/g$ to about 700 $m^2/g$, or from about 100 $m^2/g$ to about 600 $m^2/g$, or from about 100 $m^2/g$ to about 400 $m^2/g$, or from about 100 $m^2/g$ to about 300 $m^2/g$, or from about 100 $m^2/g$ to about 200 $m^2/g$, or about 100 $m^2/g$.

The density of the microcapsule of the present technology ranges from about 0.001 $g/cm^3$ to about 1.0 $g/cm^3$, or from about 0.005 g/cm³ to about 1.0 g/cm³, or from about 0.01 g/cm³ to about 1.0 g/cm³, or from about 0.02 g/cm³ to about 1.0 g/cm³, or from about 0.03 g/cm³ to about 1.0 g/cm³, or from about 0.04 g/cm³ to about 1.0 g/cm³, or from about 0.05 g/cm³ to about 1.0 g/cm³, or from about 0.06 g/cm³ to about 1.0 g/cm³, or from about 0.07 g/cm³ to about 1.0 g/cm³, or from about 0.08 g/cm³ to about 1.0 g/cm³, or from about 0.09 g/cm³ to about 1.0 g/cm³.

Methods and techniques for measuring the thickness of the shell, the surface area of and the density of microcapsules are well-known in the art.

In some embodiments, the external surfaces of the microcapsules of the present technology are functionalized. As used herein, the term "functionalized" refers to the presence of functional groups (e.g., reactive groups) on the external surface of the microcapsules. In some instances, the functional groups are present on the external surface that is facing the environment surrounding the microcapsules (i.e., the outside surface). In some instances, the functional groups are present on the external surface that is facing the inner core of the microcapsules (i.e., inside surface). In some instances, the functional groups are present on both the outside surface and the inside surface.

The functional groups may allow the microcapsules to gain affinity or adhesion to the support (e.g., textiles, fabrics, plastics, composites, rubbers, or the like). The functional groups may also serve to crosslink other molecules to the exterior surface of the microcapsules.

Examples of functional groups that may be present on the external surface of the microcapsules include, but are not limited to, hydroxyl groups, amino groups, benzylamino groups, chloropropyl groups, disulfide groups, epoxy groups, mercapto groups, methacrylate groups, and vinyl groups. Also, the external surfaces of the microcapsules may be further modified by other organofunctional groups.

In some implementations, the external surfaces of the microcapsules of the present disclosure may be electrostatically charged. In some other implementations, the external surfaces of the microcapsules of the present disclosure may be electrostatically uncharged.

In some implementations, the external surfaces of the microcapsules of the present disclosure may be polar. In some other implementations, the external surfaces of the microcapsules of the present disclosure may be non-polar.

In some embodiments, the microcapsules of the present disclosure comprise a functionalized surface layer. In some instances, the functionalized surface layer is located on the outside of the external surface. The functionalized surface layer has a thickness of about several nanometers. The functionalized surface layer comprises for example one or more organosilanes compounds, as well as other compounds.

Examples of organosilanes include, but are not limited to, 3-aminopropyltriethoxysilane, vinyl triacetoxy silane, vinyltrimethoxysilane, 3-glycidoxypropyltrimethoxysilane, 3-methacryloxy propyltrimethoxysilane, 3-chloropropyl triethoxysilane, bis-(triethoxysilylpropyl)tetrasulfane, methyltriethoxysilane, n-octyltriethoxy silane, phenyltrimethoxysilane, methacryloyloxypropyl trimethoxysilane, phenyltriethoxysilane, phenyltrimethoxysilane, glycidoxypropoxytrimethoxy silane, glycidoxypropyltriethoxysilane, mercaptopropyltriethoxysilane, mercaptopropyl trimethoxysilane, aminopropyltrimethoxysilane, 3-aminopropyltriethoxysilane, 3-(2-amino ethylamino)propyltrimethoxysilane, 3-[2-(2-amino ethylamino)ethylamino]propyl trimethoxysilane, [2(cyclohexenyl)ethyl]triethoxysilane, vinyltrimethoxysilane, vinyltriethoxysilane or a combination thereof.

The microcapsules of the present technology have a melting point which is between about 1600° C. and about 1750° C., or between about 1600° C. and about 1725° C., or between about 1600° C. and about 1700° C., or between about 1650° C. and about 1700° C. As used herein, the expression "melting point" refers to the temperature at which the microcapsule melts. In some instances, melting of the microcapsules refers to melting of the microcapsule shell.

In some embodiments, the encapsulation system of the present technology exhibits prolonged release. In some implementations of these embodiments, the prolonged release is between about 100 hours and about 800 hours, or between about 150 hours and about 800 hours, or between about 175 hours and about 800 hours, or between about 200 hours and about 800 hours, or between about 225 hours and about 800 hours, or between about 250 hours and about 800 hours, or between about 275 hours and about 800 hours, or between about 300 hours and about 800 hours, or between about 325 hours and about 800 hours, or between about 350 hours and about 800 hours, or between about 375 hours and about 800 hours, or between about 400 hours and about 800 hours, or between about 425 hours and about 800 hours, or between about 450 hours and about 800 hours, or between about 475 hours and about 800 hours, or between about 500 hours and about 800 hours, between about 100 hours and about 700 hours, or between about 150 hours and about 700 hours, or between about 175 hours and about 700 hours, or between about 200 hours and about 700 hours, or between about 225 hours and about 700 hours, or between about 250 hours and about 700 hours, or between about 275 hours and about 700 hours, or between about 300 hours and about 700 hours, or between about 325 hours and about 700 hours, or between about 350 hours and about 700 hours, or between about 375 hours and about 700 hours, or between about 400 hours and about 700 hours, or between about 425 hours and about 700 hours, or between about 450 hours and about 700 hours, or between about 475 hours and about 700 hours, or between about 500 hours and about 700 hours, between about 100 hours and about 600 hours, or between about 150 hours and about 600 hours, or between about 175 hours and about 600 hours, or between about 200 hours and about 600 hours, or between about 225 hours and about 600 hours, or between about 250 hours and about 600 hours, or between about 275 hours and about 600 hours, or between about 300 hours and about 600 hours, or between about 325 hours and about 600 hours, or between about 350 hours and about 600 hours, or between about 375 hours and about 600 hours, or between about 400 hours and about 600 hours, or between about 425 hours and about 600 hours, or between about 450 hours and about 600 hours, or between about 475 hours and about 600 hours, or between about 500 hours and about 600 hours, or at least about 100 hours, or at least about 200 hours, or at least about 300 hours, or at least about 400 hours, or at least about 500, or at least about 600 hours, or at least about 700 hours.

ii) Preparation of Encapsulation Systems

In one embodiment, the encapsulation system of the present disclosure is prepared by first obtaining a matrix of microcapsules. The matrix of microcapsules is obtained from a formulation comprising a carrier material. As intended by the present specification, the formulation represents the milieu from which the microcapsules are formed. In some instances, the formulation is a liquid formulation. In some other instances, the formulation is a dispersion of microcapsules. As used herein, the term "dispersion" refers to a system in which particles are dispersed in a continuous phase of a different composition (or state). In some instances, the dispersion is a coarse dispersion. As used herein, the expression "coarse dispersion" or "suspension" refers to a system in which minute particles are dispersed throughout a fluid from which they are easily filtered but no easily settled because viscosity or molecular interactions.

In one embodiment, the microcapsules of the present disclosure are obtained by microencapsulation techniques in which tiny particles or droplets are surrounded by a coating to give small capsules of various sizes. Microencapsulation techniques that may be used to prepare the microcapsules of the present disclosure include, but are not limited to, physical techniques, chemical techniques and physico-chemical techniques. Physical techniques include: pan coating, air-suspension coating, centrifugal extrusion, vibrational nozzle and spray-drying. Chemical techniques include: interfacial polycondensation, interfacial cross-linking, in situ polymerization, and matrix polymerization. Physico-chemical techniques include: ionotropic gelation and coacervation-phase separation. These techniques and methods are well-known in the art.

In some implementations, the microcapsules are prepared by spray-drying. In such implementations, the active agent to be encapsulated and a carrier material which is to form the microcapsule shell are homogenized as a suspension in water (the formulation).

The formulation is then fed into a spray drier, usually a tower heated to temperatures well over the boiling point of water. As the formulation enters the tower, it is atomized. Partly because of the high surface tension of water and partly because of the hydrophobic/hydrophilic interactions between the carrier material, the water, and the active agent, the atomized formulation forms micelles. The small size of the drops results in a relatively large surface area which dries quickly. As the water dries, the carrier material forms a hardened shell around the active agent.

Alternatively, the formulation can be sprayed into a partial vacuum. Since the boiling point of a solvent is the temperature at which the vapor pressure of the solvent is equal to the ambient pressure, reducing pressure in the tower has the effect of lowering the boiling point of the solvent.

In some implementations, the formulations that are used to prepare the microcapsules of the present disclosure comprise methyl salicylate as carrier material. In such implementations, the microcapsules obtained from this formulation have a shell comprising methyl salicylate. In some instances, the methyl salicylate is uniformly dispersed within the shell. In other instances, the methyl salicylate is non-uniformly dispersed within the shell. In some instances, the shell consists essentially of methyl salicylate.

In some implementations, the formulations that are used to prepare the microcapsules of the present disclosure comprise silica as carrier material. In such implementations, the microcapsules obtained from this formulation have a shell comprising silica. In some instances, the silica is uniformly dispersed within the shell. In other instances, the silica is non-uniformly dispersed within the shell. In some instances, the shell consists essentially of silica. In some instances, the silica is amorphous silica.

In some instances, the silica precursor used as carrier material is chosen from one or more of silanes having 1, 2, 3 or 4 hydrolysable groups per molecule, provided that at least one of the silanes in the mixture has at least 3 hydrolysable groups per molecule. The hydrolysable groups may be alkoxy groups (e.g. methoxy, ethoxy, propoxy, isopropoxy) or may be aryloxy groups (e.g. phenoxy), or some other hydrolysable groups. It may be for example tetramethoxysilane (TMOS), tetraethoxysilane (TEOS), tetrapropoxysilane (TPOS) or a functional trimethoxy, triethoxy or tripropoxysilane, such as aminopropylsilane, aminoethylaminopropylsilane, vinyltrimethoxysilane, 3-chloropropyltriethoxysilane, or 3-glycidoxypropyltrimethoxysilane, and combinations thereof. In some instances, the carrier material forming the shell of the microcapsules of the present technology comprises mesoporous silica. In some instances, the mesoporous silica is an ordered mesoporous silica (e.g. SBA-15, TUD-1, MCM-41, HMM-33, and FSM-16).

In some embodiments, the formulation further comprises a binding agent. A binding agent may be used in the formulations to confer stability to the formulations. Binding agents that may be useful in the present technology include, but are not limited to, polyacrylics, polyurethanes, polysiloxanes, polyvinylpyrrolidone, guar gum, resin or acrylic base or any combination thereof. Other binding agents that are useful elements in the formulations defined herein will be apparent to a person skilled in the art.

In some embodiments, the formulation further comprises a surfactant. A surfactant may be used to disperse the carrier material into water and to confer a residual charge to the microcapsules. The surfactant can be an anionic surfactant, a cationic surfactant, a nonionic surfactant, or a compatible mixture of surfactants. The surfactant also can be an ampholytic or amphoteric surfactant, which have anionic or cationic properties depending on the pH of the formulation. Examples of anionic surfactants include, without limitation, soaps, alkyl sulfates, anionic acyl sarcosinates, methyl acyl taurates, N-acyl glutamates, acyl isethionates, alkyl phosphate esters, ethoxylated alkyl phosphate esters, alkyl sulfosuccinates, trideceth sulfates, protein conden-sates, mixtures of ethoxylated alkyl sulfates, and the like. Examples of anionic non-soap surfactants include, without limitation, the alkali metal salts of an organic sulfate having an alkyl radical containing about 8 to about 22 carbon atoms and a sulfonic acid or sulfuric acid ester radical. Examples of zwitterionic surfactants include, without limitation, derivatives of aliphatic quaternary ammonium, phosphonium, and sulfonium compounds, in which the aliphatic radicals can be straight chain or branched and wherein one of the aliphatic substituents contains an anionic water-solubilizing group, e.g., carboxyl, sulfonate, sulfate, phosphate, or phosphonate. Examples of amphoteric surfactants include, without limitation, derivatives of aliphatic secondary and tertiary-amines in which the aliphatic radical can be straight chain or branched and wherein one of the aliphatic substituents contains about 8 to about 18 carbon atoms and one contains an anionic water solubilizing group, e.g., carboxyl, sulfonate, sulfate, phosphate, or phosphonate. Examples of cationic surfactants include, without limitation, stearyldimethylbenzyl ammonium chloride; dodecyltrimethyl ammonium chloride; nonyl-benzylethyldimethyl ammonium nitrate; and tetra-decylpyridinium bromide. Nonionic surfactants include, without limitation, compounds produced by the condensation or ethylene oxide groups with an organic hydrophobic compound, which may be aliphatic or alkyl aromatic in nature, for example, the polyethylene oxide condensates of alkyl phenols.

In a further specific but non-limiting example, the pH of the formulation may be in the range of from about 4 to about 10; preferably in the range of from about 6 to about 9.

iii) Active Agents

In some embodiments, the encapsulation system of the present technology encapsulates an active agent. In some implementations of these embodiments, the active agent is loaded in the inner core of the plurality of microcapsules of the encapsulation system.

The choice of the active agent is not critical and depends solely on the particular effect to be achieved once released from the encapsulation system.

Examples of active agents that may be loaded into the encapsulation system of the present disclosure include, but are not limited to, therapeutic agents, pharmaceutical agents, medicinal agent, nutraceutical agent, cosmetic agents, chemical agents, or the like. Examples of active agents, include, but are not limited to: fragrances, essential oils, caffeine, vitamins, antioxidants, UV absorbers, dyes, pigments, moisturizers, anti-cellulite agents, anti-dandruff agents, anti-inflammatory agents, antimicrobial agents, antifungal agents, warming-up agents, skin lightening agents, fire retardants, metal particles, and phase change materials (PCM).

Further examples of active agents include, but are not limited to, skin-care compounds, plant extracts, antioxidants, insect repellants, counterirritants, vitamins, steroids, antibacterial compounds, antifungal compounds, anti-inflammatory compounds, topical anesthetics, sunscreens, optical brighteners, and other cosmetic and medicinal topically effective compounds.

Examples of pharmaceutical agents include, but are not limited to: antidiarrhoeals, antihypertensives, calcium channel blockers, antiarrhythmics, antiangina agents, beta-adrenergic blocking agents; cardiotonic glycosides, adrenergic stimulants, vasodilators, antimigraine preparations, anticoagulants and thrombolytic agents, hemostatic agents, analgesics and antipyretics, neurotoxins, hypnotics and sedatives, antianxiety agents, neuroleptic and antipsychotic drugs, antidepressants, CNS stimulants, anti-alzheimer's agents, anti-Parkinson's agents, anticonvulsants, antiemetics and antinauseants, non-steroidal antiinflammatory agents, antirheumatoid agents, muscle relaxants, agents used in gout and hyperuricaemia, oestrogens, progesterone and other progestagens, antiandrogens, antioestrogens, androgens and anabolic agents, corticosteroids, pituitary hormones and their active derivatives or analogs, hypoglycemic agents, thyroid hormones, other miscellaneous hormone agents, pituitary inhibitors, ovulation inducers, diuretics, antidiuretics, obstetric drugs, prostaglandins, antimicrobials, penicillins, tetracyclines, aminoglycosides, antifungals, quinolones, sulphonamides, sulphones, other miscellaneous antibiotics, antituberculosis drugs, antimalarials, antiviral agents, anthelmintics, cytotoxic agents, weight reducing agents, agents used in hypercalcaemia, antitussives, expectorants, decongestants, bronchospasm relaxants, antihistamines, local or topical anaesthetics, stratum corneum lipids, ceramides, cholesterol and free fatty acids, neuromuscular blocking agents, smoking cessation agents, insecticides and other pesticides which are suitable for local or topical application, dermatological agents, allergens for desensitisation, nutritional agents or keratolyses, acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amidinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethasone dipropionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine and aspirin and codeine, beta-carotene, calcifediol, calcium carbonate, calcium citrate, calcium salts, candicidin, captopril, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozil, ceftazidime, cefuroxime axetil, cephalexin, cephradine, ceramic powder, chlorambucil, chloramphenicol, chlordiazepoxide, chloroquine phosphate, chlormadinone acetate, chlorothiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clindamycin hydrochloride, palmitate and phosphate, clioquinol, clofazimine, clofibrate, clomiphene citrate, clonazepam, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cyclophosphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, diclofenac epolamine, dichlorphenamide, dicloxacillin sodium, dicyclomine, dienestrol, diethylpropion hydrochlorid, diethylstilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfiram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalaphl maleate, analaprilat, ephedrine, epinephrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopropazine hydrochloride, ethotoin, ethynodiol diacetate, etidronate disodium, etoposide, eugenol, famotidine, fentanyl, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ibuprofen, ifosamide, imipramide, imipramide hydrochloride, indapamide, indomethacin, insulin, inulin, ocetamid, iodoquinol, iohexol, iopamidol, ipecac, ipodate calcium, ipodate sodium, isocarboxacid, isoetharine hydrochloride, isofluranejsoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocamithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, Ionetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measle virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenytoin, mephobarbital, meprednisone, meprobaamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, naloxone, nandrolone decanoate, nandrolone phenpropionate, naproxen, natamycin, neomycin, neomycin sulfate, neostimine bromide, niacin, nitrofurantoin, nalidixic acid, nifedipine, nitrazepam, nitrofurantoin, nitroglycerine, nitromerson, nizatidine, nonoxynol-9, norethindrone, norethindrone acetate, norfloxacin, norgestrel, nortriptyline hydrochloride, noscapine, novobiocin sodium, nystatin, opium, oxacillin sodiumn, oxamniquine, oxandrolone, oxazepam, oxprenolol hydrochloride, oxtriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin □ sulfate, polythiazide, potassium chloride, potassium citrate, potassium cluconate, potassium iodine, potassium sodiumn tartrate, povidone iodine, pralidoxime chloride, pramoxine hydrochloride, pramezam, prazepam, praziquantel, prazosin hydrochloride, prazosin hydrochloride, prednisolone, prilocaine, primaquine, primidone, probenecid, probucol, procainamide hydrochlorid, procaine hydrochloride, procarbacine hydrochloride, prochlorperazine, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamine, pyroxylin, pyrvinium pamoate, phenacetin, phenytoin, prednisone, uinidine gluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salicylic acid, salsalata, scopolamine, secobarbital sodium, selenius acid, selenium sulfate, sennaserine, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, taurine, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine, thioridazine hydrochloride, thistrepton, thiotepa, thiothixene, threonine, thyroid, ticarcillin, timolol, tioconazole, titaniumdioxide, tutanium powder, tolazamide, tolbutamide, tolmetin, tolnaftate, trazodone hydrochloride, tretinoin, triacetin, triamcinolone, triamterene, triazolam, trichorfon, trichlonnethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, trisulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefrine, silymarin, dihydroergotamine, buflomedil, etofibrate, indometacin, urea, valine, valproic acid, vancomycin hydrochloride, vasopressin, verapramil, vidarabine, vinblastine, vincristine, vitamins, warfarin, yellow fever vaccine, zinc acetate, zinc carbonate, zinc chloride, zinc gluconate, beta acetyl digoxin, piroxicam, haloperidol, ISMN, amitriptylin, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetarn, phenoxymethylpenicillin, furosemide, bromazepam, flunaridin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, primidone, clobazam, oxacepol, medroxyprogesterone, flecainid, pyridoxal-5-phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metilsulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofme, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

Examples of nutraceutical agents include components such as antioxidants, phytochemicals, hormones, vitamins such as Vitamin C and Vitamin E, pro-vitamins, minerals, microorganisms such as bacteria, fungi and yeast, prebiotics, trace elements, essential and/or highly unsaturated fatty acids such as omega-3 fatty acids and mid-chain triglycerides, nutritional supplements, enzymes, pigments, oligopeptides, dipeptides and amino acids.

The active agent may also be a protein, an enzyme, a peptide, a polysaccharide, a nucleic acid, a cell fragment, a biologically active substance, a salt, or the like. The active agent may also be a lipid such as, but not limited to, fat-soluble vitamins (e.g., vitamins A, D, E and K), ceramides in which the fatty acid components may be one or more of the following: alpha-hydroxy 6-hydroxy-4-sphingenine, alpha-hydroxy phytosphingosine, alpha-hydroxy sphingosine, ester linked omega-hydroxy 6-hydroxy-4-sphingenine, non-hydroxy phytosphingosine, non-hydroxy sphingosine, and/or ester linked omega-hydroxysphingosine and free sterols.

The active agent may have cosmetic properties such as, but not limited to: moisturizing and/or humectant, dermatological, self-tanning, anti-allergenic, anti-hair re-growth, anti-acne and/or seboregulator, anti-ageing, anti-dandruff, antimicrobial, antioxidant, antiperspirant/deo-active, anti-puffing, antistatic, anti-stretch marks, anti-tartar, anti-wrinkle, astringent, conditioning, cooling, complexing and sequestering, depilatory, depigmentors, draining, dyes, emollient, exfoliating, firming/botox-like, foaming, hair growth, healing, heating, insects repellents, lightening/whitening, myorelaxing, natural sun protector, nourishing, protective, perfumes, pearlescent agents, plant extracts, purifying, radiance, rebalance, refreshing, regenerating/revitalizing, repairing, restructuring/replenishing, softener, shining, slimming, smoothing, soothing, tensing, toning/invigorating, venotonic, vitamins etc.

The active agents may also be selected from an antifungal compound, antibacterial compounds, anti-inflammatory compounds, topical anesthetics, skin rash, skin disease, and dermatitis medications, and anti-itch and irritation-reducing compounds can be used as the active agent in the compositions of the present invention. For example, analgesics such as benzocaine, dyclonine hydrochloride, aloe vera, and the like, anesthetics such as butamben picrate, lidocaine hydrochloride, xylocaine, and the like, antibacterials and antiseptics, such as povidone-iodine, polymyxin-□-sulfate-bacitracin, zinc-neomycin sulfate-hydrocortisone, chloramphenicol, ethyl-benzethonium chloride, erythromycin, and the like; antiparasitics, such as lindane; essentially all dermatologicals, like acne preparations, such as benzoyl peroxide, erythromycin benzoyl peroxide, clindamycin phosphate, 5,7-dichloro-□-hydroxyquinoline, and the like; antiinflammatory agents, such as alclometasone dipropionate, betamethasone valer-ate, and the like; burn relief ointments, such as o-amino-p-toluenesulfonamide monoacetate, and the like; depigmenting agents, such as monobenzone; dermatitis relief agents, such as the active steroid amcinonide, diflorasone diacetate, hydrocortisone, and the like; diaper rash relief agents, such as methylbenzethonium chloride, and the like; emollients and moisturizers, such as mineral oil, PEG-4 dilaurate, lanolin oil. petrolatum, mineral wax, and the like; fungicides, such as butocouazole nitrate, haloprogin, clotrimazole, and the like, herpes treatment drugs, such as O-[(2-hydroxymethyl)-methyl] guanine; pruritic medications, such as alclo-metasone dipropionate, betamethasone valerate, iso-propyl myristate MSD, and the like; psoriasis, seborrhea, and scabicide agents, such as anthralin, methoxsalen, coal tar, and the like; steroids, such as 2-(acetyloxy)-9-fluoro-1',2',3',4'-tetrahydro-11-hydroxy-pregna-1,4-dieno-[16,17-b]naphthalene-3,20-dione, and 21-chloro-9-fluoro-1',2',3',4'-tetrahydro-b-hydroxypregna-1,4-dieno-[16,17-b]naphthalene-3,20-dione.

The topically-active agent also can be a plant extract or natural oil. Non-limiting plant extracts are those obtained from alfalfa, aloe vera, amla fruit, angelica root, anise seed, apple, apricot, artichoke leaf, asparagus root, banana, barberry, barley sprout, bee pollen, beet leaf, toil-berry fruit, birch leaf, bitter melon, black currant, leaf, black pepper, black walnut, blueberry, burdock, carrot, cayenne, celery seed, cherry, chickwood, cola nut, corn silk, cranberry, dandelion root, elderberry, eucalyptus leaf, flax oil powder, ginger root, gingko leaf, ginseng, goldenrod, goldenseal, grape, grapefruit, guava, hibiscus, juniper, kiwi, kudzu, lemon, licorice root, lime, malt, marigold, myrrh, olive leaf, orange fruit, orange peel, oregano, papaya fruit, papaya leaf, passion fruit, peach, pear, pine bark, plum, pomegranate, prune, raspberry, rice bran, rhubarb root, rosemary leaf, sage leaf, spearmint leaf, St. John's wart, strawberry, sweet cloves, tangerine, violet herb, watercress, watermelon, willow bark, wintergreen leaf, witch hazel bark, yohimbe, and yucca root.

The concentration of active agent in the microcapsules of the present disclosure may be between about 20% and about 90% of the total weight of the microcapsule, between about 20% and about 75%, of the total weight of the microcapsule or between about 25% and about 55% of the total weight of the microcapsule; or between about 30% and about 50% of the total weight of the microcapsule, or about 40% and about 50% of the total weight of the microcapsule; or the concentration of active agent in the microcapsules of the present disclosure is about 25%, about 30%, about 35%, about 40%, about 45% about 50% or about 55% of the total weight of the microcapsule.

iv) Support Systems

In another embodiment, the present technology relates to supports comprising the encapsulation system as defined herein. As used herein, the term "support" refers to materials onto which the encapsulation system is applied and from which the active agent is released. As used herein the expression "treated support" refers to a support comprising the encapsulation system of the present technology, whereas the expression "untreated support" refers to a support that does not comprise the encapsulation system of the present technology.

Examples of supports include, but are not limited to, fibrous textiles including natural fibers either vegetal (e.g., cotton, linen, jute) or animal (e.g., wool and silk) as well as mineral fibers (e.g., asbestos and viscose); chemical fibers either synthetic or artificial like polyester, nylon, acetate, polypropylene and rayon; paper and paper products; product made from composites; products made from wood or wood by-products, such as furniture materials and doors; products made from carbon fiber, products made from glass fiber, synthetic foam, such as polyethylene, polystyrene and polyurethane foam. Textiles may be woven, knitted or machine-knitted, or be present as a composite material (non-woven textile). In the case of composite materials, the fabric is not produced by wrap and weft or stitch formation, but by interlocking and/or cohesive and/or adhesive bonding of textile fibers. Non-woven fabrics are loose materials produced from spun fibers or filaments, in most cases made of polypropylene, polyester or viscose, the cohesion of which is generally provided by the fibers intrinsically holding together. In this regard, the individual fibers may have a preferred orientation (oriented or cross-laid non-woven fabrics), or be unoriented (entangled non-woven fabrics). The non-woven fabrics may be mechanically bonded by needle punching, stitching, or entangling by means of strong water jets. Adhesively bonded non-woven fabrics are produced by gluing the fibers together with liquid binding agents (for example, acrylate polymers, SBR/NBR, polyvinyl ester, polyurethane dispersions), or by melting or dissolving so-called binder fibers that are added to the non-woven fabric during its production. Non-woven material may be obtained from, for example, viscose, cotton, cellulose, elastane, jute, hemp, sisal, silk, wool, polypropylene, polyester, polyethylene terephthalate (PET), aramide, nylon, polyvinyl derivatives, polyurethanes, polylactide, polyhydroxyalkanoate, cellulose esters and/or polyethylene, and also mineral fibers, such as glass fibers or carbon fibers. Examples of fabrics also include blends of dual or multiple fibers such as, but not limited to, polyester/elastane blends, polyamids, polyamide/elastane blends, cotton/polyester/elastane blends, polyacrylonitriles, acetates, modal, lyocell and linens.

The support may also be made of polyesters, polyester/elastane blends, polyamides, polyamide/elastane blends, cotton, cotton/elastane blends, cotton/polyester blends, cotton/polyester/elastane blends, polyacrylonitriles, cellulose acetates, modal, lyocell, linens and/or wool. Supports of the present disclosure may also comprise polyurethane.

In some implementations, the microcapsules of the present disclosure are applied to textile materials using one or more binder agents. A number of approaches can be used to apply microcapsules to textile materials using binder agents. For example, in one approach, a textile material is placed in a bath containing both microcapsules and binder agents followed by heating or drying of the textile material. Other approaches involve contacting textile materials with binder agents before adding microcapsules. Yet other approaches involve coating microcapsules with binders prior to applying them to textile materials. Within any of these approaches, the degree to which microcapsules adhere to a particular textile material is typically a function of the process used but can also be influenced by the binder agent selected.

v) Methods for Impregnating the Encapsulation System on a Support

In some embodiments, the present disclosure provides supports having the encapsulation system impregnated therein. To obtain supports having the encapsulation system impregnated therein, a formulation comprising the encapsulation system is applied to the support. Additives may be added to the formulation such as binders, crosslinking agents, organic or inorganic pigments and fillers, antifoaming agents and/or other surfactants, and viscosity-controlling agents/thickeners, to improve or enhance the adherence of the encapsulation system to the support.

Examples of binders that may be added to the formulation include, but are not limited to: i) water-soluble polymers, such as polyvinyl alcohol, carboxymethyl cellulose, starch and modified starches, xanthanes, alginates, and other natural gums; ii) synthetic latexes, such as polyacrylate latexes, styrene-butadiene, polyvinyl-acetate, ethylene-vinyl acetate copolymers; iii) synthetic resins, such as such as urea- and melamine-formaldehyde resins, dimethylol ethylene urea, dimethylol dihydroxy ethylene urea, dimethylol propylene urea, polyurethane and epoxy resins, vinyl acetate resins; iv) synthetic rubbers, such as polyurethanes, nitrile and chloroprene rubbers; and v) silicones.

Various techniques may be used in order to apply the formulation to supports (e.g., textiles or fabrics) including, but not limited to: coating with an air knife, rod coater or other tools of the like; impregnation or immersion; printing techniques, such as screen-, photographic-, electrostatic-, pressure-transfer, thermal transfer and inkjet printing; spraying on the surface of supports; inclusion of the encapsulation system into the fibers of textiles during the spinning process, such as polyester, nylon or modacryl fiber material; and incorporation into polymer foams, coatings and multilayer composites that are placed or inserted into selected parts of the textile.

Supports falling within the scope of the present technology can be used in a variety of applications, including but not limited to clothing, athletic apparel, intimate apparel, hosiery (such as sheer pantyhose and socks), ready-to-wear, swimwear, towels and blanket, beddings, hats. Supports treated with the encapsulation system of the present technology may have improved washfastness (wash durability) and ability to retain the desired effect provided by the microencapsulated material. For example, when the microencapsulated material is a fragrance, fabrics falling within the scope of the present disclosure have the ability to retain the fragrance, even after numerous washings and extended wear by the end user.

In some embodiments, the encapsulation system of the present disclosure is used to impart or to provide properties and/or functionalities to a support. In some implementations of these embodiments, the active agents encapsulated in the encapsulation system are responsible for imparting and/or providing the properties and/or functionalities to the support. In some other implementations of these embodiments, the components of the shell as well as the active agents are responsible for imparting and/or providing the properties and/or functionalities to the support. For example, the encapsulation system of the present disclosure may be used to encapsulate dyes and pigments for textile dyeing and printing, for microencapsulating thermochromics or photochromic materials for application onto textiles; for microencapsulating catalysts and enzymes for special textile effects; for microencapsulating fire retardants; for microencapsulating agents for textile sizing and adhesive bonding; for microencapsulating blowing agents and expandable microcapsules for leather substitutes; for microencapsulating textile water proofing agents; for microencapsulating textile softening and antistatic compositions; for microencapsulating ingredients in textile detergents; for microencapsulating enzymes; for microencapsulating bleaching agents and whiteners; for microencapsulating fragrances and perfumes; for microencapsulating animal repellents; for microencapsulating antimicrobial, disinfectant and deodorant components; for microencapsulating bioactive medical and cosmetic textiles with microencapsulated ingredients; for microencapsulating decontaminants, filters and odor absorbers; for microencapsulating active thermal control; for microencapsulating.

vi) Release of the Active Agent

Microcapsules are released from the treated support when the microcapsules are subjected to degradation and/or detachment caused by one or more stimuli or when the treated support is subjected to stimuli that cause degradation of the microcapsules or simply when the microcapsules are detached from the support.

The overall physical structure of the microcapsules is affected by stimulus which weakens or breaks the interactions between the microcapsules and the support so as to release or detach the microcapsules from the support. A stimulus does not affect each microcapsule in the encapsulation system evenly giving rise to a progressive erosion, destruction and/or release of the microcapsules from the support.

Stimuli that cause detachment of the microcapsules from the support include, but are not limited to, physical stimuli, chemical stimuli or electrical stimuli. A physical stimulus may be such as a mechanical contact with the treated support, rubbing or vibration of the support, heat that may or may not be involved in mechanical contact. A chemical stimulus may be such as the exposure to a chemical agent, a change in pH, a change in salt concentration, exposure to microbes or toxin secreted by microbes, a change in temperature and a change in humidity or the like.

Release of the content of the microcapsules may occur in the presence of one or more types of stimuli. Examples of such stimuli include, but are not limited to: i) external pressure which breaks the microcapsule wall and releases the core; ii) inner pressure which may break the shell of the microcapsules, which may occur if the inner core comprises active agents which, under special conditions (e.g., UV light), decompose into gaseous components; iii) abrasion of the shell which can lead to release of the core active agent; iv) heat which causes melting of the shell at a specifically designed temperature; v) dissolution, microcapsules may dissolve in a specific solvent, sometimes only at a selected pH value of the washing cycle; and vi) enzymatic degradation.

In some embodiments, the treated support of the present technology retains the microcapsules of the encapsulation system for a prolonged length of time, thereby ensuring a prolonged release of the active agent from the treated support. In some implementations, the prolonged length of time during which the treated support retains microcapsules is between about 100 hours and about 800 hours, or between about 150 hours and about 800 hours, or between about 175 hours and about 800 hours, or between about 200 hours and about 800 hours, or between about 225 hours and about 800 hours, or between about 250 hours and about 800 hours, or between about 275 hours and about 800 hours, or between about 300 hours and about 800 hours, or between about 325 hours and about 800 hours, or between about 350 hours and about 800 hours, or between about 375 hours and about 800 hours, or between about 400 hours and about 800 hours, or between about 425 hours and about 800 hours, or between about 450 hours and about 800 hours, or between about 475 hours and about 800 hours, or between about 500 hours and about 800 hours, between about 100 hours and about 700 hours, or between about 150 hours and about 700 hours, or between about 175 hours and about 700 hours, or between about 200 hours and about 700 hours, or between about 225 hours and about 700 hours, or between about 250 hours and about 700 hours, or between about 275 hours and about 700 hours, or between about 300 hours and about 700 hours, or between about 325 hours and about 700 hours, or between about 350 hours and about 700 hours, or between about 375 hours and about 700 hours, or between about 400 hours and about 700 hours, or between about 425 hours and about 700 hours, or between about 450 hours and about 700 hours, or between about 475 hours and about 700 hours, or between about 500 hours and about 700 hours, between about 100 hours and about 600 hours, or between about 150 hours and about 600 hours, or between about 175 hours and about 600 hours, or between about 200 hours and about 600 hours, or between about 225 hours and about 600 hours, or between about 250 hours and about 600 hours, or between about 275 hours and about 600 hours, or between about 300 hours and about 600 hours, or between about 325 hours and about 600 hours, or between about 350 hours and about 600 hours, or between about 375 hours and about 600 hours, or between about 400 hours and about 600 hours, or between about 425 hours and about 600 hours, or between about 450 hours and about 600 hours, or between about 475 hours and about 600 hours, or between about 500 hours and about 600 hours, or at least about 100 hours, or at least about 200 hours, or at least about 300 hours, or at least about 400 hours, or at least about 500, or at least about 600 hours, or at least about 700 hours.

In some other implementations, the prolonged length of time during which the active agent is released from the treated support is between about 100 hours and about 800 hours, or between about 150 hours and about 800 hours, or between about 175 hours and about 800 hours, or between about 200 hours and about 800 hours, or between about 225 hours and about 800 hours, or between about 250 hours and about 800 hours, or between about 275 hours and about 800 hours, or between about 300 hours and about 800 hours, or between about 325 hours and about 800 hours, or between about 350 hours and about 800 hours, or between about 375 hours and about 800 hours, or between about 400 hours and about 800 hours, or between about 425 hours and about 800 hours, or between about 450 hours and about 800 hours, or between about 475 hours and about 800 hours, or between about 500 hours and about 800 hours, between about 100 hours and about 700 hours, or between about 150 hours and about 700 hours, or between about 175 hours and about 700 hours, or between about 200 hours and about 700 hours, or between about 225 hours and about 700 hours, or between about 250 hours and about 700 hours, or between about 275 hours and about 700 hours, or between about 300 hours and about 700 hours, or between about 325 hours and about 700 hours, or between about 350 hours and about 700 hours, or between about 375 hours and about 700 hours, or between about 400 hours and about 700 hours, or between about 425 hours and about 700 hours, or between about 450 hours and about 700 hours, or between about 475 hours and about 700 hours, or between about 500 hours and about 700 hours, between about 100 hours and about 600 hours, or between about 150 hours and about 600 hours, or between about 175 hours and about 600 hours, or between about 200 hours and about 600 hours, or between about 225 hours and about 600 hours, or between about 250 hours and about 600 hours, or between about 275 hours and about 600 hours, or between about 300 hours and about 600 hours, or between about 325 hours and about 600 hours, or between about 350 hours and about 600 hours, or between about 375 hours and about 600 hours, or between about 400 hours and about 600 hours, or between about 425 hours and about 600 hours, or between about 450 hours and about 600 hours, or between about 475 hours and about 600 hours, or between about 500 hours and about 600 hours, or at least about 100 hours, or at least about 200 hours, or at least about 300 hours, or at least about 400 hours, or at least about 500, or at least about 600 hours, or at least about 700 hours.

EXAMPLES

Example 1: Preparation of an Encapsulation System

Dry microcapsules of various sizes were obtained from a liquid formulation containing the carrier material and a composition of the active agent by nebulizing the liquid formulation in a flow of air against the current and at a fixed temperature in order to dry the aerosol and to obtain solid microcapsules at the bottom of the nebulization chamber. Table 1A indicates the ingredients that were used to obtain the liquid formulation of the carrier material and Table 1B indicates the ingredients that were used to prepare the composition of active agents.

TABLE 1A

| Carrier material |
| --- |
| INGREDIENTS |
| Octylphenol Ethoxylate |
| Diphenyl phosphate |
| Pluronic ® PE 10300 (3250 g/mol polypropylene glycol and 30% polyethylene glycol) |
| Tergito ™ NP9 (Nonylphenol Ethoxylate) |
| Methyl salicylate |
| Water |

TABLE 1B

| Active ingredient composition | |
| --- | --- |
| INGREDIENTS | WT % IN LIQUID FORMULA |
| *Prunus amygdalus dulcis* oil | 50-75 |
| *Gaultheria procumbens* leaf oil | 10-20 |
| *Butyrospermum parkii* butter | 10-20 |
| Propylene glycol dicaprylate/dicaprate | 5-10 |
| *Piper Nigrum* Fruit Oil | 1-5 |
| *Arnica Montana* Extract | 1-5 |
| Tocopheryl acetate | 0.1-1 |
| *Helianthus Annuus* (Sunflower) Seed Oil | 0.1-1 |
| Water | 1-5 |
| Oil | 1-5 |

Example 2: Preparation of a Treated Support

Figure 3:
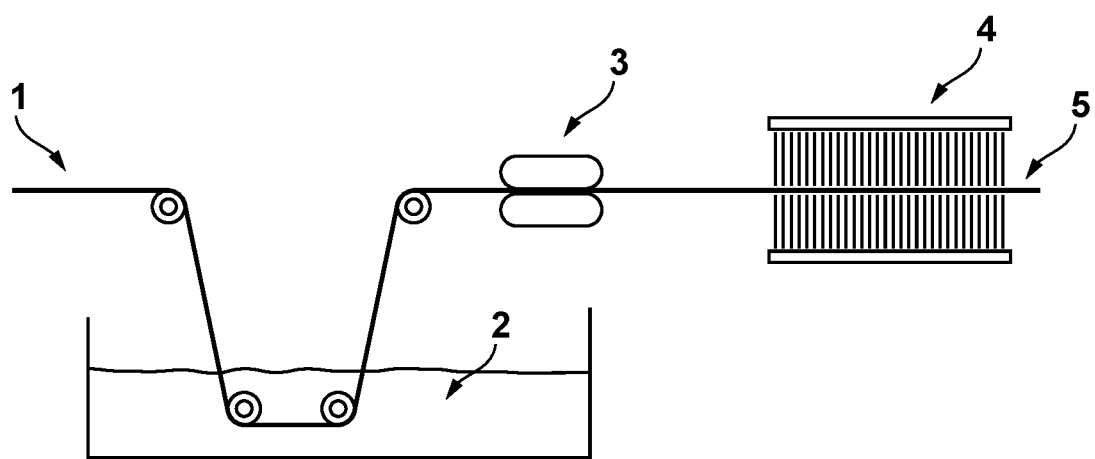
FIG. 3 shows a schematic representation of a padding process according to one embodiment of the present disclosure wherein the encapsulation system is applied onto a textile support, wherein: (1) represents untreated textile; (2) represents a pad bath comprising a formulation of the encapsulation system (+/−binder); (3) represents a compression zone; (4) represents a drying and a heating treatment.

The technique of padding was used for application of the encapsulation system prepared as outlined in Example 1 on a textile support (e.g., cotton or nylon). The textile was soaked in a pad bath comprising a formulation of microcapsule (e.g., dispersion) at a concentration of $7\times10^9$ microcapsules/ml (i.e., approximately 100 g/l). A surfactant and a binder were also added in the dispersion so as to improve the fixation of the microcapsules to the fibers of the textile. Once the textile support was impregnated with the formulation of microcapsules, it was passed through 2 compressor cylinders with a pressure set at 1 bar. The textile support was then subjected to a heat treatment at 134° C. for 3 minutes to fix the microcapsules to the support. The resulting treated support comprised 26 grams of formulation per 150 grams of textile. FIG. 3 shows a schematic representation of the padding process for application of the microcapsules on the support. The following first and second passes were optionally performed after the compression to ensure that a maximum of microcapsules were properly fixed to the support.

First pass of the treated textile in the oven: Heating from 20° C. to 250° C. at 10° C./min; Holding for 1 min at 250° C.; Cooling from 250° C. to 20° C. at 20° C./min; and Hold for 1 min at 20° C. Second pass of the treated textile in the oven: Heating from 20° C. to 250° C. at 10° C./min; Holding for 1 min at 250° C.; Cooling from 250° C. to 20° C. at 20° C./min; and Hold for 1 min at 40° C.

Example 3: Prolonged Release of Active Agent from Treated Knee Pad

Microcapsules comprising wintergreen essential oils and arnica extracts as active agents were prepared as outlined in Example 1. The loaded microcapsules were then applied to the interior of a knee pad using the method outlined in Example 2. The treated knee pad was worn by three subjects suffering from arthrosis of the knee and experiencing pain throughout the day (evaluated at 8-9 on the pain scale).

The subjects experienced relief of the pain after one hour of wearing the treated knee pad. The relief lasted for about 32 days (about 768 hours). FIG. 4 shows the prolonged and sustained release of the microcapsules from the treated knee pad. These results suggest that microcapsules were retained on the treated knee pad for a period of at least about 32 days and that over this period, microcapsules and/or active agents were continuously released from the treated support to give rise to a prolonged release of the active agent.

Example 4: Prolonged Release of Active Agent from Treated Textiles

Microcapsules comprising wintergreen essential oils and arnica extracts as active agents were prepared as outlined in Example 1. The loaded microcapsules were then applied to textile pads using the method outlined in Example 2 and the treated textile pads were worn by the subjects experiencing pain at different body parts. FIG. 7 as well as Table 2 indicates the body parts that were treated as well as the efficiency of the treatment. The treated pad was worn by the subject during 4 hours per day for a period of 4 weeks.

TABLE 2

Subjects treated with a treated pad to relief pain

|  | Knee | Elbow | Shoulder | Back | Ankle | Wrist |
| --- | --- | --- | --- | --- | --- | --- |
| Number of treated subjects | 65 | 54 | 35 | 34 | 27 | 27 |
| Number of treated subject showing positive results | 63 | 54 | 32 | 30 | 27 | 27 |
| % Efficiency | 97% | 100% | 91% | 88% | 100% | 100% |

Treated textile pads were further worn by subjects experiencing various types of pain. FIG. 8 as well as Table 3 indicates the type of pain experienced by the subjects and the efficiency of the treatment. The treated pad was worn by the subject during 4 hours per day for a period of 4 weeks.

TABLE 3

Subjects suffering from the indicated pain and treated with a support comprising the encapsulation system to relief pain

|  | Osteoarthritis | Tendinitis | Sprain | Low back pain | Meniscus | Sciatica | Partial tear of tendon |
| --- | --- | --- | --- | --- | --- | --- | --- |
| Number of treated subjects | 85 | 84 | 7 | 15 | 12 | 10 | 9 |
| Number of treated subject showing positive results | 82 | 83 | 7 | 15 | 9 | 7 | 9 |
| % Efficiency | 96% | 99% | 00% | 100% | 75% | 70% | 100% |

Example 5: Pilling Resistance of Treated Support

A pilling resistance test according to the ASTM D3512 method was performed on a treated textile support (92% polyester, 8% elastane) prepared as outlined in Example 2 to assess the influence of wear on the treated textile and on the detachment of the microcapsules from the treated textile. According to the ASTM D3512 method, 60 minutes of testing is equivalent to 300 hours of wear and 120 minutes of testing is equivalent to 600 hours of wear. After each cycle of the method, electron microscopy (Hitachi TM-100) was performed on the textile to assess detachment of the microcapsules. The results obtained show that microcapsules were still present on the fibers of the textile after 180 minutes of testing. FIG. 5 shows the presence of microcapsules attached on the fibers of the textile after 180 minutes of testing.

Example 6: Resistance of Treated Support to Wash/Dry Cycles

To assess the resistance of the encapsulation system of the present disclosure to washing/drying cycles, the treated textile (92% polyester, 8% elastane) prepared as outlined in Example 2 was subjected to a series of washing/drying cycles (5, 10, 15 and 20 washing/drying cycles) which were carried out according to the parameters of CAN/CGSB N 58-2004 (washing 40° C.; drying delicate setting 60° C. with 5 min cooling period at the end of drying). Following the series of indicated washing/drying cycles, the treated textile was analyzed by electron microscopy (Hitachi TM-100) to assess detachment of the microcapsules from the textile.

Figure 6E:
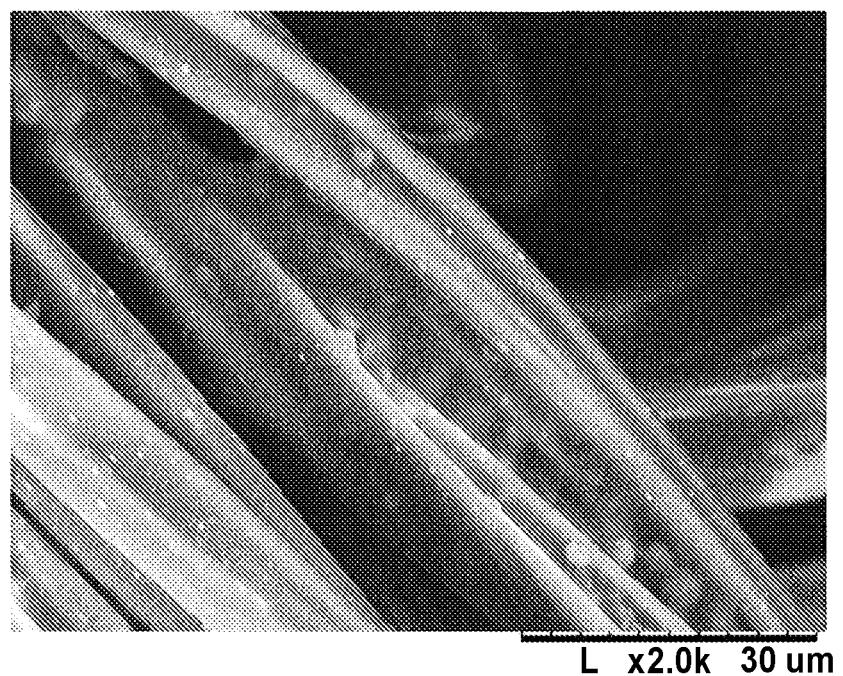

FIG. 6A shows the treated textile prior to the initial cycle of washing/drying. FIG. 6B shows the treated textile after 5 cycles of washing/drying. FIG. 6C shows the treated textile after 10 cycles of washing/drying. FIG. 6D shows the treated textile after 15 cycles of washing/drying. FIG. 6E shows the treated textile after 20 cycles of washing/drying. FIG. 6E indicates the presence of microcapsules of a size inferior to 10 microns remaining on the fibers of the textile after 20 cycles of washing/drying.

Any feature of any embodiment discussed herein may be combined with any feature of any other embodiment discussed herein in some examples of implementation.

Certain additional elements that may be needed for operation of certain embodiments have not been described or illustrated as they are assumed to be within the purview of those skilled in the art. Moreover, certain embodiments may be free of, may lack and/or may function without any element that is not specifically disclosed herein.

Although various embodiments and examples have been presented, this was for the purpose of describing, but not limiting, the invention. Various modifications and enhancements will become apparent to those skilled in the art and are within the scope of the invention, which is defined by the appended claims.

All documents referred to herein are incorporated by reference.

The invention claimed is:

1. An encapsulation system for delivery of an active agent, the encapsulation system comprising a matrix of microcapsules, the microcapsules having a microcapsule shell obtained from a formulation consisting of methyl salicylate, at least one surfactant, diphenyl phosphate, and water, the microcapsule shell surrounding a core-forming space, wherein a first portion of microcapsules in the matrix of microcapsules has an average diameter of from about 0.1 microns to about 10 microns; a second portion of the microcapsules has an average diameter of from about 10 microns to about 100 microns; and a third portion of the microcapsules has an average diameter of from about 100 microns to about 500 microns; and wherein the active agent is encapsulated in the microcapsules; and wherein the surface area of the microcapsules is from about 100 $m^2/g$ to about 1000 $m^2/g$.

2. A support for delivery of an active agent to a subject, the support comprising an encapsulation system distributed in at least a portion of the support, the encapsulation system comprising a matrix of microcapsules, the microcapsules having a microcapsule shell obtained from a formulation consisting of methyl salicylate, at least one surfactant, diphenyl phosphate, and water, the microcapsule shell surrounding a core-forming space, wherein a first portion of microcapsules in the matrix of microcapsules has an average diameter of from about 0.1 microns to about 10 microns; a second portion of the microcapsules has an average diameter of from about 10 microns to about 100 microns; and a third portion of the microcapsules has an average diameter of from about 100 microns to about 500 microns; wherein the active agent is encapsulated in the microcapsules; wherein the surface area of the microcapsules is from about 100 $m^2/g$ to about 1000 $m^2/g$; and wherein the support releases the active agent for at least about 100 hours.

3. The support as defined in claim 2, wherein the support releases the active agent for at least about 200 hours, or at least about 300 hours, or at least about 400 hours, or at least about 500, or at least about 600 hours, or at least about 700 hours.

4. The support as defined in claim 2, wherein the release of the active agent is sustained for at least about 100 hours.

5. The support as defined in claim 4, wherein the release of the active agent is sustained for at least about 200 hours, or at least about 300 hours, or at least about 400 hours, or at least about 500, or at least about 600 hours, or at least about 700 hours.

6. The support as defined in claim 2, wherein the release of the active agent is constant for at least 100 hours.

7. The support as defined in claim 6, wherein the release of the active agent is constant for at least about 200 hours, or at least about 300 hours, or at least about 400 hours, or at least about 500, or at least about 600 hours, or at least about 700 hours.

8. The support as defined in claim 2, wherein the support is a textile.

9. The support as defined in claim 2, wherein the support is a fabric.

10. The support as defined in claim 2, wherein the support is a polymer.

* * * * *